(12) United States Patent
Schwartz

(10) Patent No.: US 6,436,071 B1
(45) Date of Patent: Aug. 20, 2002

(54) INTRAVASCULAR SYSTEMS FOR CORPOREAL COOLING

(75) Inventor: Arthur E. Schwartz, Englewood, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/330,428

(22) Filed: Jun. 8, 1999

(51) Int. Cl.[7] .................................................. A61F 7/12
(52) U.S. Cl. .................. 604/113; 604/247; 604/102.01; 604/102.02; 604/102.03
(58) Field of Search ........................... 604/113, 102.01, 604/102.02, 102.03, 247

(56) References Cited

U.S. PATENT DOCUMENTS

| | | |
|---|---|---|
| 380,626 A | 4/1888 | Hamilton |
| 697,181 A | 4/1902 | Smith |
| 2,112,737 A | 3/1938 | Dodge |
| 2,257,369 A | 9/1941 | Davis |
| 3,220,414 A | 11/1965 | Johnston |
| 3,504,674 A | 4/1970 | Swenson |
| 3,885,561 A | 5/1975 | Cami |
| 3,888,249 A | 6/1975 | Spencer |
| 3,897,790 A | 8/1975 | Magilton et al. |
| 3,931,822 A | 1/1976 | Marici |
| 4,149,535 A | 4/1979 | Volder |
| 4,224,929 A * | 9/1980 | Furihata ........................ 128/5 |
| 4,445,892 A * | 5/1984 | Hussein et al. ............. 604/101 |
| 4,447,227 A | 5/1984 | Kotsanis |
| 4,549,879 A | 10/1985 | Groshong et al. |
| 4,573,966 A | 3/1986 | Weikl et al. |
| 4,863,441 A | 9/1989 | Lindsay et al. |
| 4,892,099 A * | 1/1990 | Ohkawa et al. ............. 606/194 |
| 5,019,042 A | 5/1991 | Sahota |
| 5,021,044 A | 6/1991 | Sharkawy |
| 5,106,363 A | 4/1992 | Nobuyoshi |
| 5,147,332 A | 9/1992 | Moorehead |
| 5,180,364 A | 1/1993 | Ginsburg |
| 5,188,596 A * | 2/1993 | Condon et al. ............. 604/101 |
| 5,207,655 A | 5/1993 | Sheridan |
| 5,224,938 A | 7/1993 | Fenton, Jr. |
| 5,234,405 A | 8/1993 | Klatz et al. |
| 5,364,376 A * | 11/1994 | Horzeski et al. ............ 604/280 |
| 5,626,564 A | 5/1997 | Zhan et al. |
| 5,709,654 A | 1/1998 | Klatz et al. |
| 5,738,666 A | 4/1998 | Watson et al. |
| 5,826,621 A * | 10/1998 | Jemmott ...................... 137/853 |
| 5,827,222 A | 10/1998 | Klatz et al. |
| 5,868,703 A * | 2/1999 | Betolero et al. ............ 604/102 |
| 6,042,559 A * | 3/2000 | Dobak, III ...................... 604/7 |
| 6,056,723 A * | 5/2000 | Donlon ........................ 604/102 |
| 6,090,069 A * | 7/2000 | Walker .................. 604/102.03 |

\* cited by examiner

*Primary Examiner*—Linda C. M. Dvorak
*Assistant Examiner*—Jocelyn Ram
(74) *Attorney, Agent, or Firm*—Reed Smith LLP

(57) ABSTRACT

A catheter for intravascular corporeal cooling comprises an elongated tubular member having at least one lumen extending therethrough for providing cooled blood, an inflatable annular balloon positioned on the outer surface of the elongated tubular member, and a pressure reliever positioned in the external wall of the elongated tubular member and proximal to the annular inflatable balloon, wherein when the pressure of blood within a lumen reaches a predetermined value, the pressure reliever opens to permit fluid to be released from the elongated tubular member. In other embodiments of the invention the catheter may have two or more inflatable annular balloons that are separately inflatable and/or the catheter has an insulative outer annular member.

37 Claims, 6 Drawing Sheets

INTRAVASCULAR SYSTEMS FOR CORPOREAL COOLING

FIELD OF THE INVENTION

This invention is directed to intravascular systems for corporeal cooling. More particularly, this invention is directed to catheter systems that have features that are especially useful for cooling organs, tissue, or limbs.

BACKGROUND OF THE INVENTION

It has been found that cooling of the central nervous system provides many advantages in dealing with neurological problems. Beneficial results have been obtained from hypothermia of the intracranial structures in surgical treatment of certain brain tumors, cerebrovascular lesions such as aneurysms and hemangiomas, and head injuries. Hypothermia of the intracranial structures results in a decrease in brain volume and cerebral blood flow, as well as the arrest of cerebral edema when present. Furthermore, when the tissue of the central nervous system cools, there is a decrease in oxygen consumption and, therefore, greater protection against anoxia during deficient or arrested circulation. In addition, the resistance of brain tissue to surgical trauma is markedly increased and surgical bleeding is easy to control. Thus, local or regional hypothermia of the central nervous system is effective as a therapeutic technique, per se, as a surgical aid and also as a post-operative technique.

Cerebral hypothermia in the past has been brought about by cooling the entire body (surface cooling and intravascular perfusion), cooling the vascular supply to the brain, regional hypothermia by extracorporeal intravascular perfusion, or by the use of cold capsules or ice applied directly to the cerebral hemispheres. Systemic hypothermia by intravascular perfusion requires an additional major surgical procedure and carries with it a number of complications. A serious complication sometimes experienced through the use of systemic hypothermia (surface or intravascular) is ventricular fibrillation and cardiac asystole, which is attributable to the lower temperature tolerance of heart neuromuscular elements, as compared with central nervous system tissue.

There are a number of intravascular systems that are presently used for corporeal cooling, especially brain cooling. However, it has been found that there are certain disadvantages when such systems are used, and there is a definite need for improved systems.

OBJECTS OF THE INVENTION

It is an object of the invention to provide intravascular systems useful for corporeal cooling, especially cooling the brain or other organs, such as the kidneys.

It is also an object of the invention to provide an intravascuar system for corporeal cooling that has a pressure dependent valve.

It is a further object of the invention to provide a method for treating stroke patients where the patients are treated by brain cooling shortly after the stroke event to minimize insult and/or damage.

It is yet a further object of the invention to provide an intravascular system having balloons with variable inflation.

It is an additional object of the invention to provide an insulated intravascular system.

It is a still further object of the invention to provide an intravascular system having variable fenestration.

It is likewise an object of the invention to provide an intravascular system for cooling organs, tissue, or limbs.

It is a yet further object of the invention to provide an intravascular system for delivering drugs or other fluids to a desired corporeal location.

These and other objects of the invention will become more apparent from the discussion below.

SUMMARY OF THE INVENTION

In an intravascular brain cooling procedure, a catheter is advanced into the common carotid artery and the distal tip of the catheter is positioned within the internal carotid artery. Preferably the distal tip of the catheter has one or more inflatable balloons or other structures to obstruct the annular space between the outer surface of the catheter and the inner surface of the internal carotid artery. Cooled blood is provided to the brain through one or more lumens in the catheter.

A catheter for corporeal cooling may have a pressure sensitive valve to provide relief in the event of pressure build-up within the catheter. Also, the catheter may be insulated to avoid systemic cooling and related cardiac complications. At the proximal section of a corporeal cooling catheter system where the patient's blood is removed for cooling, an outer catheter sheath may comprise variable fenestrations to facilitate blood withdrawal. Optionally a catheter according to the invention may have one or more pressure sensors to sense blood pressure within or without the catheter.

In addition, it has been found that brain cooling may be beneficial when applied to stroke patients. Further, cooling a kidney by providing cooled blood into a renal artery can be effective in treating renal failure.

DETAILED DESCRIPTION OF THE INVENTION

Figure 1:
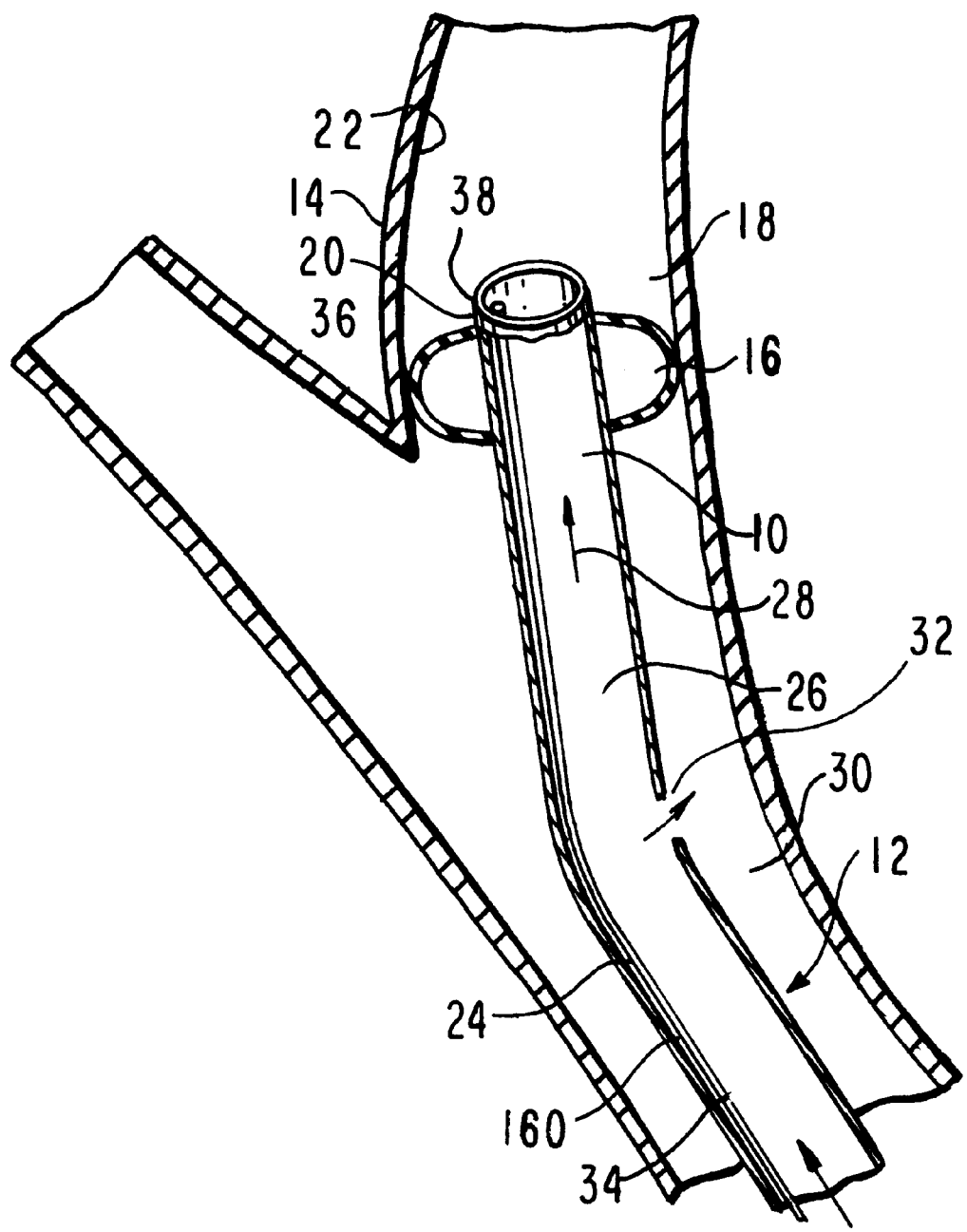
FIG. 1 is a schematic representation of an embodiment of the invention having a pressure-dependent valve.

The invention herein can perhaps best be appreciated from the drawings. In FIG. 1, the distal end 10 of an intravascular corporeal catheter 12 is positioned within the internal carotid artery 14. Distal end 10 comprises at least one inflatable balloon 16 to seal the annular space 18 between the outer surface 20 of catheter 12 and the inner surface 22 of internal carotid artery 14.

Catheter 12 comprises two or more lumens, at least an inflation lumen 24 for inflation of balloon 16 and a lumen 26 for providing cooled blood in the direction of arrow 28. Proximal to distal end 10 and preferably within common carotid artery 30 is a pressure-dependent valve or relief means 32. Valve 32, which is intended to be in the wall of, or otherwise in fluid communication with, lumen 26, is intended to rupture in the event the pressure of blood within lumen 26 exceeds a pre-determined value, to avoid any problem associated with supplying blood under too much pressure to the brain.

Valve 32 can be comprised of any of several known one-way valving means, which include, for example, slits, fissures, caps, flaps, friable membranes, and the like.

Figure 2:
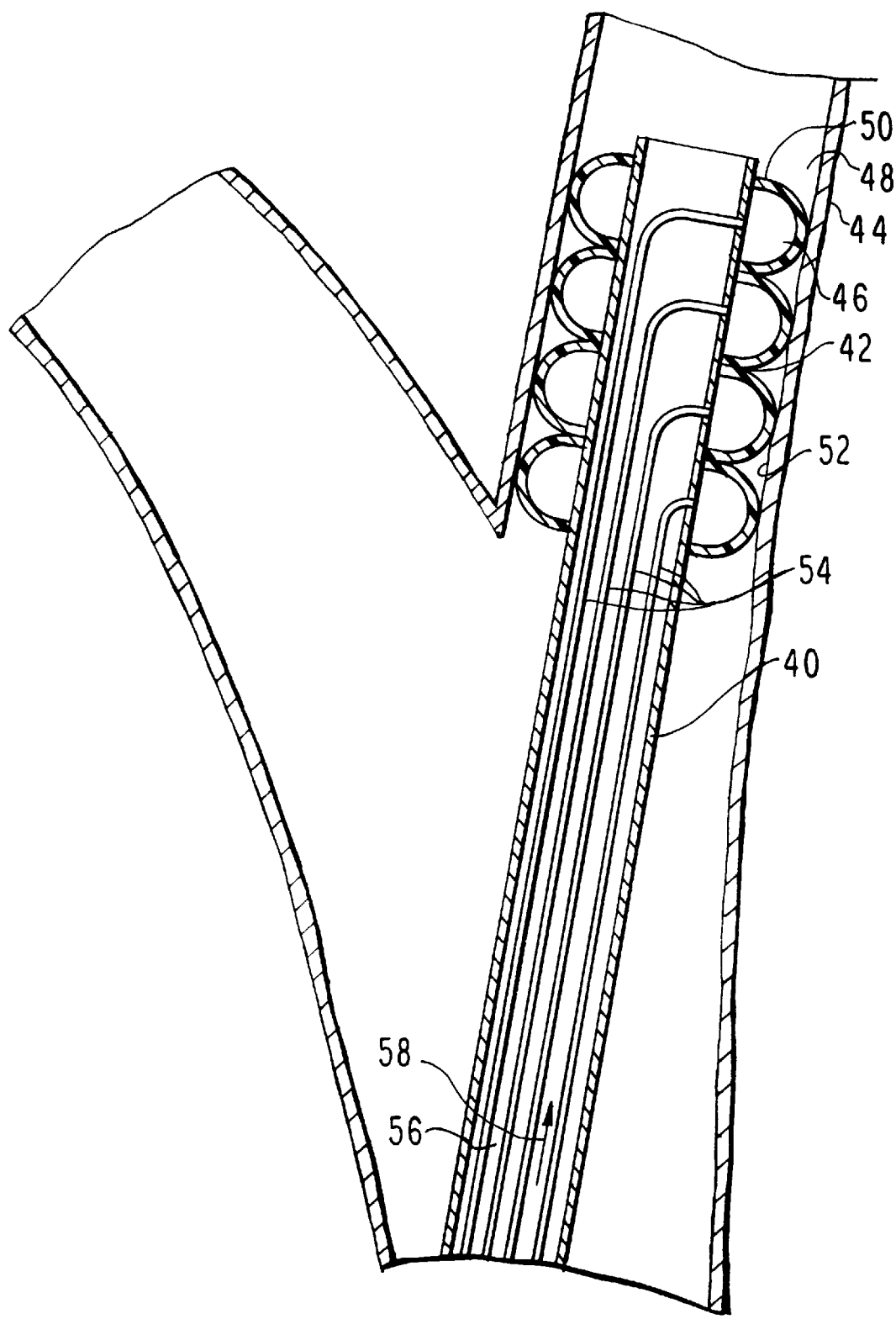
FIG. 2 is a schematic representation of an embodiment of the invention having variable inflation.

The intravascular corporeal catheter 40 shown in FIG. 2 comprises a distal section 42 positioned within internal carotid artery 44. Distal section 42 comprises two or more, preferably 3 or 4, inflatable balloons 46 positioned in the annular space 48 between the outer surface 50 of catheter 40 and the inner surface 52 of internal carotid artery 44. Preferably each balloon 46 has a separate inflation lumen 54 extending in the proximal direction to an inflator (not shown). However, it is within the scope of the invention that two or more, adjacent or non-adjacent, balloons could be in fluid communication with a single inflation lumen. The inflator is capable of inflating balloons 46 in a desired sequence and/or pressure to obstruct flow within annular space 48. An example of inflator technology useful according to the invention is described in U.S. Pat. No. 3,931,822, incorporated herein by reference.

Catheter 40 also comprises at least one lumen 56 to provide cooled blood to the brain in the direction of arrow 58.

Figure 3:
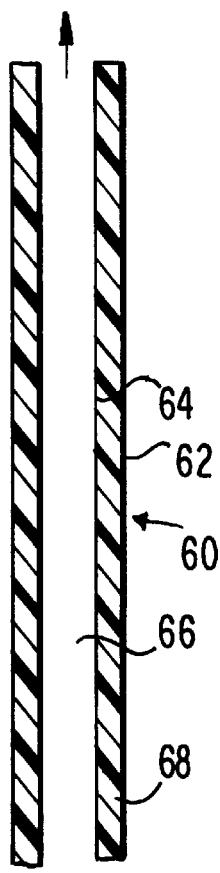
FIG. 3 is a partially cross-sectional view of an embodiment of the invention wherein the intravascular system is insulated.

FIG. 3 is a cross-sectional view of a portion of a catheter 60 especially useful for intravascular corporeal cooling. Catheter 60 comprises an outer cylindrical wall 62 and an inner cylindrical wall 64, which inner wall preferably comprises at least one lumen 66 for providing cooled blood. The annular or substantially annular space 68 between inner wall 64 and outer wall 62 should provide insulative properties. For example, the annular space may comprise a fluid, preferably a gaseous fluid such as air, or other insulation material such as any of the known synthetic insulation materials, silica gel, or thermal insulating materials such as are disclosed in U.S. Pat. Nos. 2,967,152, 3,007,596, and 3,009,600, all of which are incorporated herein by reference. The insulation used should not restrict, or should have only minimal impact upon, the flexibility of catheter 60.

Figure 4:
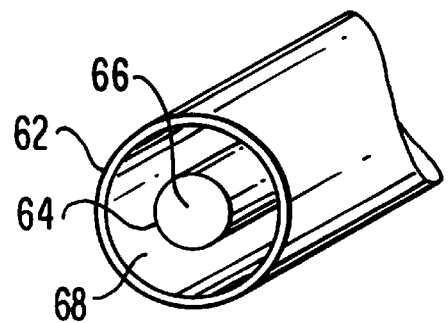
FIG. 4 is an oblique view of one end of the intravascular system shown in FIG. 3.

A schematic, oblique cross-section of catheter 60 is shown in FIG. 4. Annular space 68 between outer wall 62 and inner wall 64 can be filled with fluid or insulation.

Figure 5:
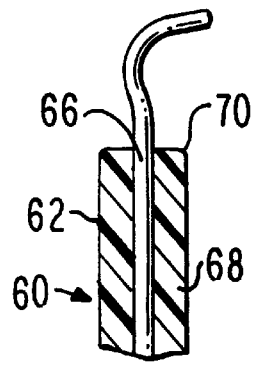
FIG. 5 is a partially cross-sectional view of an embodiment of the invention wherein intravascular system is partly insulated.
Figure 6:
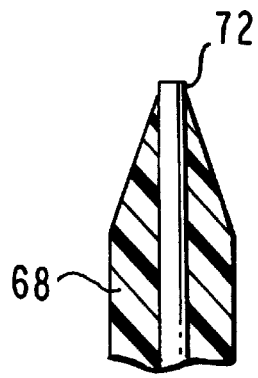
FIGS. 6 and 7 are each a partially cross-sectional view of a portion of an insulated intravascular catheter.
Figure 7:
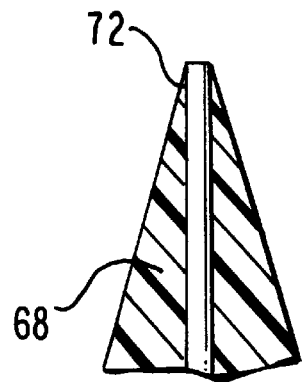

The insulation construction described may extend for the entire length or for only a portion of an intravascular corporeal catheter. For example, as shown in FIG. 5, the annular space 68 may terminate at surface 70 and inner wall 64 will continue as an uninsulated catheter. Also, as shown in FIGS. 6 and 7, either or both of the proximal and distal ends, especially the distal end, of catheter 60, then the annular space 68 may taper to a distal point 72 of catheter 60.

Figure 8:
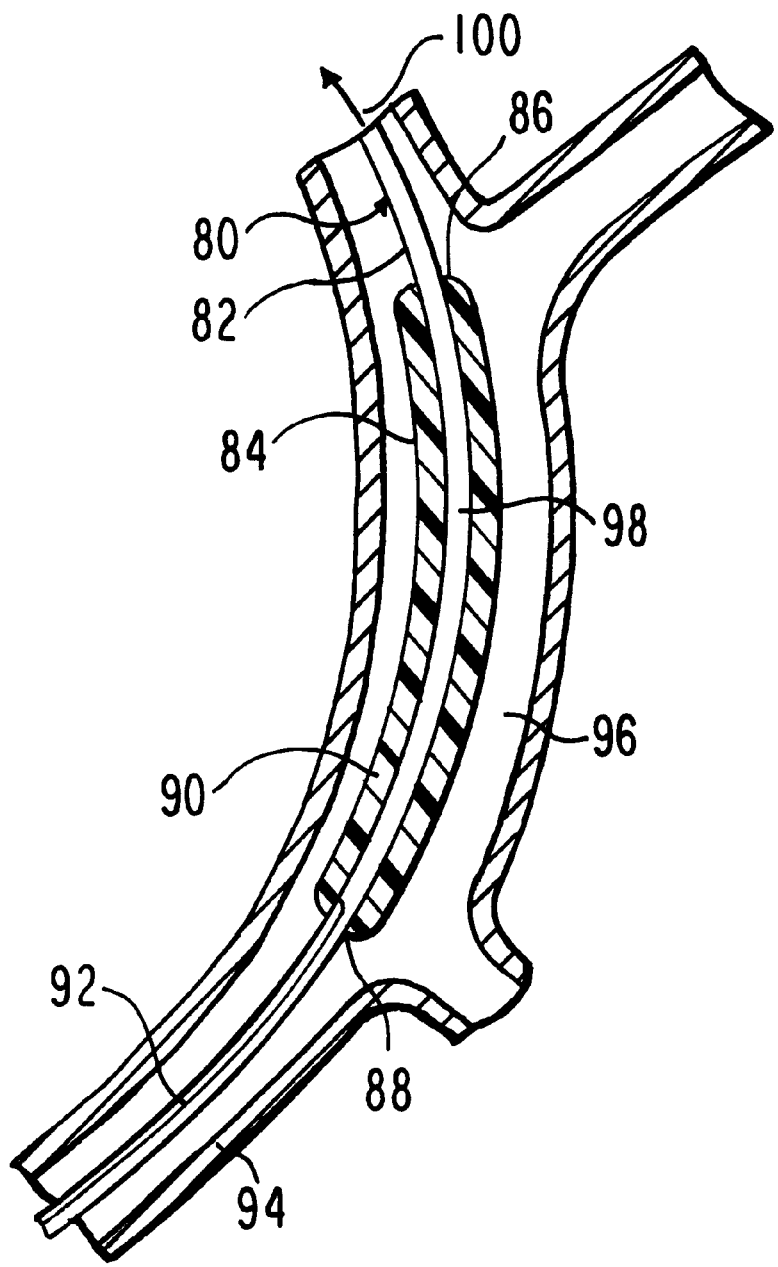
FIG. 8 is a partially cross-sectional view of another embodiment of an insulated intravascular system according to the invention.

According to the embodiment of the invention shown in FIG. 8, an intravascular corporeal catheter 80 comprises a longitudinal tubular member 82 that has a partially co-extensively extending inflatable insulation member 84. Insulation member 84 is sealed to the extension of tubular member 82 at distal position 86 and proximal position 88, the interior 90 of inflatable insulation member 84 being in fluid connection through inflation lumen 92 with an inflator (not shown). Inflation member 84 is intended to have a low profile and facilitate insertion through the femoral artery 94 into the aorta 96, which is larger in diameter. Once inflation member 84 is positioned within aorta 96, inflation member 84 is inflated to provide insulation when cooled blood is passed through one or more lumens 98 in catheter 82 in the direction of arrow 100.

Intravascular corporeal catheters 12, 40, 60, and 80 as shown in FIGS. 1 to 8 are especially useful in brain cooling, where cooled blood is provided to a patient's brain. However, it is within the scope of the invention that each of said catheters may have broader use in cooling other organs, tissue, or limbs, or even in the delivery of substances such as pharmaceuticals or other agents to desired sites within a patient's body.

Figure 9:
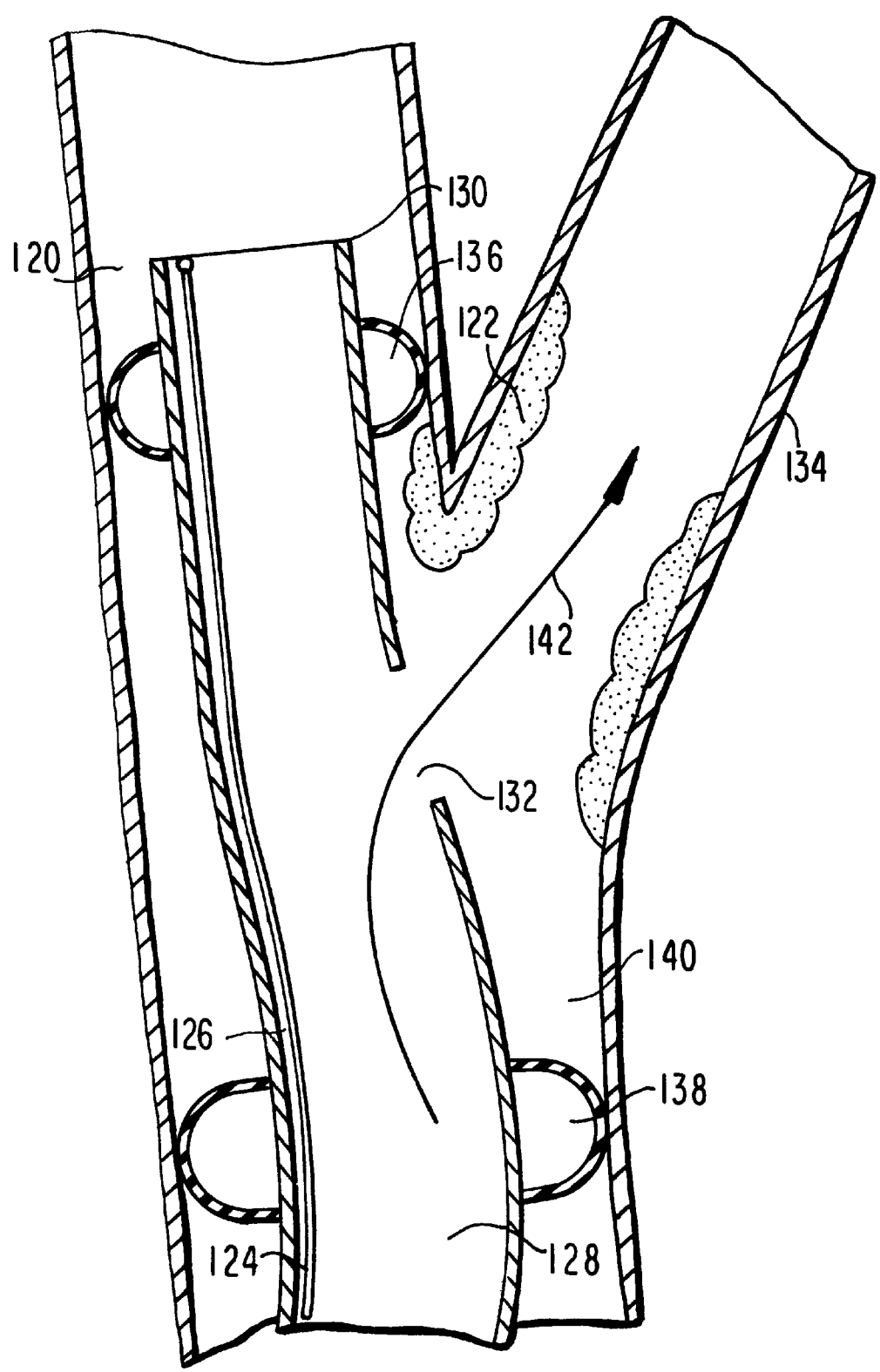
FIG. 9 is a partly cross-sectional view of another embodiment of the invention.

FIG. 9 is a schematic representation of an embodiment of the invention particularly useful when the internal carotid artery 134 has plaque 122. A catheter 124 comprises a through lumen 126 for passage of a guidewire (not shown) and optionally blood for the external carotid artery. Catheter 124 also comprises at least one blood flow lumen 128 having a closed distal end 130 and a lateral opening 132 for providing cooled blood to the internal carotid artery 134. Inflatable balloons 136, 138 are positioned in the external carotid artery 120 and the common carotid artery 140, respectively. Cooled blood flows in the direction of arrow 142 through lateral opening 132 and within plaque 122 into internal carotid artery 134.

It is within the scope of the invention that a corporeal cooling catheter could have additional capability, such as pressure and/or temperature measurement. For example, in FIG. 1 catheter 12 may comprise a lumen 34 having a distal end 36. Distal end 36 could be open or optionally it could comprise an element 38 which is a transducer or diaphragm, optionally with fiber optic cable 160. A number of known techniques for measuring pressure and/or temperature can be used, including, but not limited to, a configuration where there is no lumen 34 and a transducer element 38 could be electrically connected via wires (not shown) to a controller (not shown). Also, there could be more then one pressure and/or temperature sensor, located at different positions on the distal section of a corporeal cooling catheter. For example, in FIG. 1, a pressure sensor element 38 could be located where shown or on the surface of catheter 10 distal or proximal to balloon 16. For representative examples of pressure and/or temperature sensor technology, see, for example, U.S. Pat. Nos. 4,487,206, 4,641,654, 5,427,114, 5,456,251, 5,325,865, 5,647,847, 5,866,821, and 5,899,927, all of which are incorporated herein by reference. Measurement of pressure is of particular interest. Flow and pressure greater than the desired range may lead to brain injury, and flow and pressure less than the desired range may be insufficient to achieve organ cooling.

Figure 10:
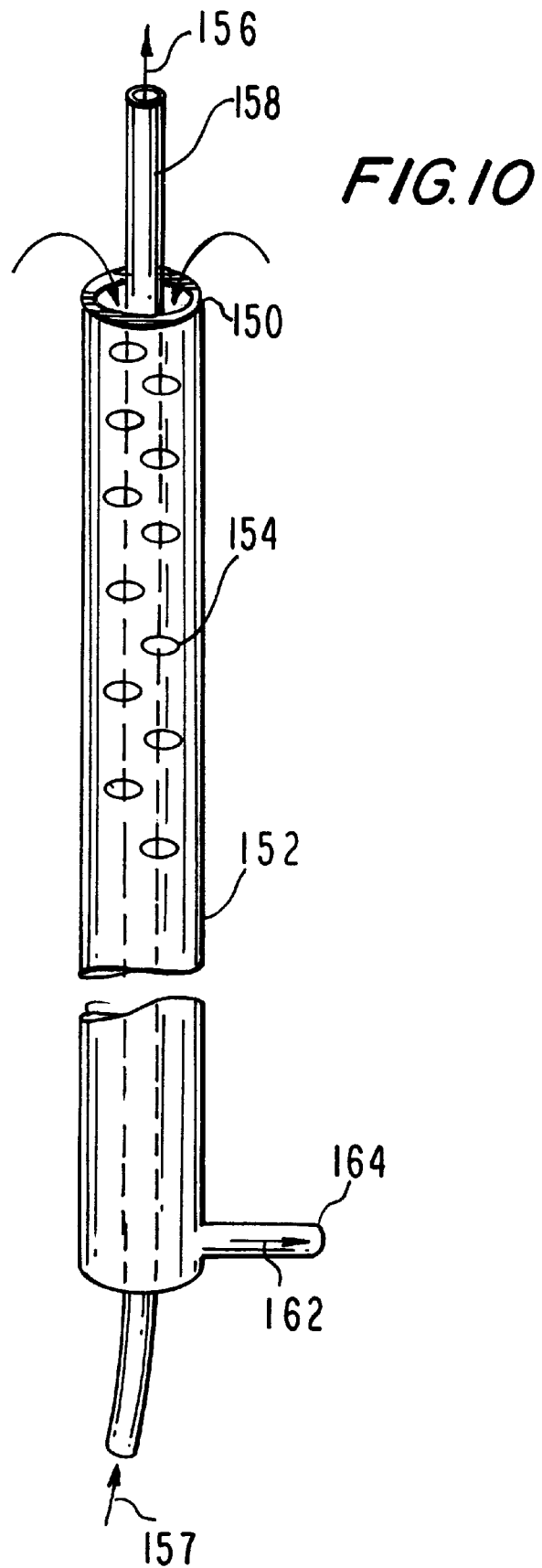
FIG. 10 is an oblique, schematic view of an embodiment of the invention having fenestrations.

As part of the brain cooling process blood has to be removed from the patient for cooling and then returned to the patient. Preferably this can be done in a single site to minimize trauma to the patient. It is known to use a catheter set wherein an outer catheter extends only shortly distally into the patient's artery, blood is removed proximally through an annular space between the outer catheter and a distally-extending inner catheter, and cooled blood is returned through the inner catheter. However, since the available surface area for proximal blood flow is only a profile corresponding to said annular space, there are sometimes problems that develop due to pressure or fluid build-up in this area. According to an embodiment of the invention, and as shown in FIG. 10, the distal end 150 of an introducer sheath 152 contains fenestrations 154 of varied, uniform, or variable size. Cooled blood is returned in the direction represented by arrow 156 through catheter 158. Body temperature blood enters introducer sheath 152 in the direction of the arrows at distal end 150 through fenestrations 154. Fenestrations 154 preferably are circular, substantially circular, or oval, and have a diameter or effective diameter of from about 0.5 to 5 mm. It is within the scope of the invention that introducer sheath 152 comprise two concentric, slidably and/or rotably arranged tubular members so that the member and/or size of the fenestrations can be varied by rotating or sliding the outer of the two concentric members.

Another aspect of the invention concerns the use of brain cooling to treat stroke victims. When the cerebral vasculature of a stroke victim is flushed with cooled blood, the insult or damage normally associated with a stroke is either minimized or avoided altogether. The effectiveness of the brain cooling will depend upon several factors, including the severity of the stroke, the length of time after the stroke that the patient is treated, the duration of the treatment, the temperature of the cooled blood, the volume of cooled blood administered, etc. For example, the duration of the treatment could be from about 6 to 18 hours, the temperature of the cooled blood could be from about 16° to 24° C., and the volume of the cooled blood could be from about 100 to 900 ml/min. It is significant that the flow rate and/or pressure of the cooled blood should be adjusted so that the blood pressure in the stroke patient's internal carotid artery is slightly greater than systemic blood pressure.

It would be advantageous to treat a stroke victim as soon as possible after the stroke, it being understood that the treatment is likely to be most effective if the patent is treated within 12 hours after the stroke. It is preferred that brain cooling be administered no more than 12 hours after the stroke, although treatment up to 18 hours or even more may still be of limited effectiveness, dependent upon all the factors involved.

In a preferred embodiment of the invention the brain cooling is administered in conjunction with a thrombolytic agent such as TPA, heparin, streptokinase, or the like. The thrombolytic agent could be administered according to known protocols prior to, during, and/or subsequent to the brain cooling. Similarly, in the event that surgical or endovascular intervention is indicated in a stroke victim, brain cooling could be administered in conjunction with such a procedure.

To effect vascular brain cooling according to the invention, normal procedures are followed. First, a guide catheter is established and then the distal tip of a brain cooling catheter is advanced through the femoral artery, through the aorta, into the common carotid artery. Then, dependent upon which embodiment of the invention described herein is employed, the distal tip of the brain cooling catheter is then positioned in either the internal carotid or the external carotid artery, whereupon the inflation balloons are inflated. Cooled blood is perfused through one or more lumens in the brain cooling catheter to the internal carotid artery.

According to one embodiment of the invention, cooled blood is provided to one or more kidneys to treat, minimize, or avoid renal failure. A catheter according to the invention, preferably a catheter such as described in FIG. 1, is advanced through the aorta and then into the left or right renal artery. The distal tip of the catheter is then positioned in the left or right renal artery at a point between the aorta and the left or right kidney, respectively. Once the annular balloon is inflated, cooled blood perfuses the kidney. While preferably one kidney is treated at a time, possibly sequentially, it is within the scope of the invention that both kidneys could be treated simultaneously, dependent upon the equipment used. The conditions of treatment in terms of blood temperature, blood flow, and duration would be similar to those for brain cooling, with the exception that such renal treatment is likely to be of less duration.

Any of the known devices for cooling blood during cardiac procedures could be used. One example of such available equipment to cool the patient's blood is the SARNS TCM water bath available from the SARNS Corp. of Ann Arbor, Mich. Such a water bath is used with a cardiopulmonary bypass machine such as the BP40, available from Biomedicus, Minneapolis, Minn. Details regarding brain cooling procedures are readily available See, for example, A. E. Schwartz et al., "Isolated Cerebral Hypothermia by Single Carotid Artery perfusion of Extracorporeally Cooled Blood in Baboons", *Neurosurgery*, Vol. 39, No. 3, September 1996, pp. 577–582, and A. E. Schwartz et al., "Selective Cerebral Hypothermia by Means of transfemoral Internal Carotid Artery Catherization", *Radiology*, Vol. 201, No. 2, November 1996, pp. 571–572, both of which are incorporated herein by reference.

The catheters described above comprise conventional bio-compatible materials used in the catheter field. For example, the catheters may be comprised of suitable low-friction bio-compatible polymers such as, for example, extruded polyethylene polyvinyl chloride, polystyrene, or polypropylene or copolymers thereof. Inflatable balloons would be comprised of polymers or polypropylenes or copolymers thereof. The catheters may have a hardness of, for example, from 60 to 90 Shore A duramter. The inner elongated tubular members of the invention would typically have an i.d. of from about 7.5 to 10.5 F and an o.d. of from about 8 to 11 F, where an outer tubular member would typically have an i.d. of from about 8.5 to 11.5 F and an o.d. of from about 9 to 12 F.

The catheters useful according to the invention may optionally have one or more radiopaque markers in their distal sections, the markers preferably comprising rings comprised of tantalum, platinum, or gold. Also, the catheter may have any of the well-known anti-thrombotic or lubricious coatings.

The preceding specific embodiments are illustrative of the practice of the invention. It is to be understood, however, that other expedients known to those skilled in the art or disclosed herein, may be employed without departing from the spirit of the invention or the scope of the appended claims.

What is claimed is:

1. A catheter for intravascular corporeal cooling which comprises:
    an elongated tubular member having proximal and distal sections, at least first and second lumens extending therethrough, an outer surface, and an outer wall,
    an inflatable annular balloon positioned on the outer surface of the elongated tubular member and in fluid communication with a lumen for inflation, and
    pressure relief means positioned in the outer wall of the elongated tubular member and proximal to the annular inflatable balloon,
wherein at least the first lumen can provide cooled blood in the distal direction and distal to the inflatable annular balloon, and when the pressure of fluid within the first lumen reaches a predetermined value, the pressure relief means opens to permit fluid to be released from the elongated tubular member.

2. The catheter of claim 1, wherein the annular balloon is in fluid communication with an inflation lumen extending longitudinally through the tubular member.

3. The catheter of claim 1, which comprises at least one additional inflatable annular balloon.

4. The catheter of claim 3, wherein each inflatable annular balloon is in fluid communication with an inflation lumen.

5. The catheter of claim 1 which also comprises a pressure sensor at or adjacent to the distal end of the catheter.

6. The catheter of claim 1 which has been adapted for brain cooling.

7. The catheter of claim 1, wherein at least one lumen is in fluid communication with a source of cooled blood.

8. The catheter of claim 1, wherein at least one lumen is in fluid communication with a liquid pharmaceutical source.

9. A catheter for intravascular corporeal cooling which comprises:
an elongated tubular member having proximal and distal sections, at least first and second lumens extending therethrough, an outer surface, and an outer wall;
an inflatable annular balloon positioned on the outer surface of the elongated tubular member and in fluid communication wit a lumen for inflation; and
pressure relief means comprising a one-way valve positioned in the outer wall of the elongated tubular member and proximal to the annular inflatable balloon,
wherein at least the first lumen can provide cooled blood in the distal direction and distal to the inflatable annular balloon, and wherein when the pressure of fluid within the first lumen reaches a predetermined value, the pressure relief means opens to permit fluid to be released from the elongated tubular member.

10. The catheter of claim 9, wherein the annular balloon is in fluid communication with an inflation lumen extending longitudinally through the elongated tubular member.

11. The catheter of claim 9, which comprises at least one additional inflatable annular balloon.

12. The catheter of claim 11, wherein each inflatable annular balloon is in fluid communication with an inflation lumen.

13. The catheter of claim 9 which also comprises a pressure sensor at or adjacent to the distal end of the elongated tubular member.

14. The catheter of claim 9 which is useful for brain cooling.

15. The catheter of claim 9, wherein at least one lumen is in fluid communication with a source of cooled blood.

16. The catheter of claim 9, wherein at least one lumen is in fluid communication with a liquid pharmaceutical source.

17. A catheter for intravascular corporeal cooling which comprises:
an elongated tubular member having proximal and distal sections, at least first and second lumens extending therethrough, an outer surface, and an outer wall;
an inflatable annular balloon positioned on the outer surface of the elongated tubular member and in fluid communication with a lumen for inflation;
pressure relief means positioned in the outer wall of the elongated tubular member and proximal to the annular inflatable balloon, and
a pressure sensor at or adjacent to the distal end of the elongated tubular member,
wherein at least the first lumen can provide cooled blood in the distal direction and distal to the inflatable annular balloon, and wherein when the pressure relief means opens to permit to be released from the elongated tubular member.

18. The catheter of claim 17, wherein the pressure relief means comprises an elongated fissure.

19. The catheter of claim 17, wherein the annular balloon is in fluid communication with an inflation lumen extending longitudinally through the elongated tubular member.

20. The catheter of claim 17, which comprises at least one additional inflatable annular balloon.

21. The catheter of claim 20, wherein each inflatable annular balloon is in fluid communication with an inflation lumen.

22. The catheter of claim 17 which is useful for brain cooling.

23. The catheter of claim 17, wherein at least one lumen is in fluid communication with a source of cooled blood.

24. The catheter of claim 17, wherein at least one lumen is in fluid communication with a liquid pharmaceutical source.

25. A catheter for intravascular corporeal cooling which comprises:
an elongated tubular member having proximal and distal sections, at least first and second lumens extending therethough, an outer surface, and an outer wall;
an inflatable annular balloon positioned on the outer surface of the elongated tubular member and in fluid communication with a lumen for inflation; and
pressure relief positioned in the outer wall of the elongated tubular member and proximal to the annular inflatable balloon,
wherein at least the first lumen can provide cooled blood in the distal direction and distal to the inflatable annular balloon, wherein at least one lumen is in fluid communication with a source of cooled blood, and wherein when the pressure of fluid within the first lumen reaches a predetermined value, the pressure relief means opens to permit fluid to be released from the elongated tubular member.

26. The catheter of claim 25, wherein the pressure relief means comprises an elongated fissure.

27. The catheter of claim 25, wherein the annular balloon is in fluid communication with an inflation lumen extending longitudinally through the elongated tubular member.

28. The catheter of claim 25, which comprises at least one additional inflatable annular balloon.

29. The catheter of claim 28, wherein each inflatable annular balloon is in fluid communication with an inflation lumen.

30. The catheter of claim 25 which is useful for brain cooling.

31. The catheter of claim 25, wherein at least one lumen is in fluid communication with a liquid pharmaceutical source.

32. A catheter for intravascular coporeal cooling which comprises:
an elongated tubular member having proximal and distal sections, at least first and second lumens extending therethrough, an outer surface, and an outer wall;
an inflatable annular balloon positioned on the outer surface of the elongated tubular member and in fluid communication with a lumen for inflation; and
pressure relief means positioned in the outer wall of the elongated tubular member and proximal to the annular inflatable balloon,
wherein at least the first lumen can provide cooled blood in the distal direction and distal to the inflatable annular balloon, wherein at least one lumen is in fluid communication with a liquid pharmaceutical source, and wherein when the pressure of fluid within the first lumen reaches a predetermined value, the pressure relief means opens to permit fluid to be released from the elongated tubular member.

33. The catheter of claim 32, wherein the pressure relief means comprises an elongated fissure.

34. The catheter of claim 32, wherein the annular balloon is in fluid communication with an inflation lumen extending longitudinally through the elongated tubular member.

35. The catheter of claim 32, which comprises at least one additional inflatable annular balloon.

36. The catheter of claim 35, wherein each inflatable annular balloon is in fluid communication with an inflation lumen.

37. The catheter of claim 32 which is useful for brain cooling.

* * * * *